United States Patent
Radcliffe et al.

(10) Patent No.: US 11,026,498 B2
(45) Date of Patent: Jun. 8, 2021

(54) SYSTEM, APPARATUS AND METHOD FOR CODING CAPS FOR DIFFERENT BOTTLE SIZES

(71) Applicant: ULTRAFAB, INC., Farmington, NY (US)

(72) Inventors: Alan P. Radcliffe, Victor, NY (US); Alan J. Demello, Newmarket, NH (US)

(73) Assignee: ULTRAFAB, INC., Farmington, NY (US)

( * ) Notice: Subject to any disclaimer, the term of this patent is extended or adjusted under 35 U.S.C. 154(b) by 0 days.

(21) Appl. No.: 16/884,676

(22) Filed: May 27, 2020

(65) Prior Publication Data

US 2020/0305583 A1      Oct. 1, 2020

Related U.S. Application Data

(63) Continuation of application No. PCT/US2019/034761, filed on May 30, 2019.

(60) Provisional application No. 62/678,055, filed on May 30, 2018.

(51) Int. Cl.
| | |
|---|---|
| *A45F 3/16* | (2006.01) |
| *B65D 47/06* | (2006.01) |
| *B65D 47/32* | (2006.01) |
| *B65D 51/24* | (2006.01) |

(52) U.S. Cl.
CPC .............. *A45F 3/16* (2013.01); *B65D 47/06* (2013.01); *B65D 47/32* (2013.01); *B65D 51/245* (2013.01); *A45F 2003/163* (2013.01); *B65D 2203/00* (2013.01); *B65D 2205/00* (2013.01)

(58) Field of Classification Search
CPC ... A45F 3/16; A45F 2003/163; B65D 51/245; B65D 47/06; B65D 47/32; B65D 2205/00; B65D 2203/00
USPC .......... 215/230, 309, 387–389; 220/705–709
See application file for complete search history.

(56) References Cited

U.S. PATENT DOCUMENTS

| | | | |
|---|---|---|---|
| 1,577,539 A | 3/1926 | Polk | |
| 2,096,585 A | 10/1937 | Hoeter | |
| 2,684,674 A * | 7/1954 | Archer | A61J 1/1462 215/247 |

(Continued)

OTHER PUBLICATIONS

Ultrafab, Inc., Bioreactor Single Use Kits, https://www.ultrafab.com/product/bioreactor-single-use-kits/, printed Mar. 23, 2018.

(Continued)

*Primary Examiner* — James N Smalley
(74) *Attorney, Agent, or Firm* — Kenneth J. Lukacher Law Group

(57) ABSTRACT

A plurality of caps are provided each with a visual coding of color and/or indicia for use with different sizes of bottles at least in accordance with a height of the bottles from a closed bottom end to an open top end for engaging each of the caps. Each of the caps has a tube mounted to, or through, an aperture extending through a top closed end of the cap to extend a selected length enabling one end of the tube to reach or extend along an interior surface of the bottom end of any of the bottles of the height to which the cap is coded for use therewith. The other end of tube is extendable to a bioreactor container. Each of the caps has another tube or port to another aperture of the cap to provide an air vent with an optional air filtering device.

30 Claims, 14 Drawing Sheets

(56) References Cited

U.S. PATENT DOCUMENTS

| | | | |
|---|---|---|---|
| 3,045,879 A | | 7/1962 | Daly |
| 4,195,059 A | | 3/1980 | Whitcher et al. |
| 4,700,861 A | | 10/1987 | Neward |
| 4,701,101 A | * | 10/1987 | Sapoff .................. B01J 8/002 222/229 |
| 4,714,173 A | * | 12/1987 | Ruiz .................. A47G 19/2266 220/709 |
| 4,993,573 A | * | 2/1991 | Freidel .................. B01L 3/08 215/276 |
| 5,048,705 A | | 9/1991 | Lynd et al. |
| 5,199,604 A | | 4/1993 | Palmer et al. |
| 5,558,214 A | | 9/1996 | Brundidge |
| 5,586,588 A | * | 12/1996 | Knox .................. B67D 1/04 141/18 |
| 5,711,917 A | | 1/1998 | Juranas et al. |
| 6,322,242 B1 | | 11/2001 | Lang et al. |
| 6,341,628 B1 | | 1/2002 | Burson |
| 6,745,505 B2 | | 6/2004 | Moran |
| 7,604,778 B2 | | 10/2009 | Dause |
| 8,028,446 B2 | | 10/2011 | Moran |
| 8,286,812 B2 | | 10/2012 | Buczkowski |
| 8,657,157 B2 | | 2/2014 | Blinn |
| 9,272,896 B2 | | 3/2016 | Unger et al. |
| 9,403,629 B2 | | 8/2016 | Accurso |
| 9,908,665 B2 | | 3/2018 | Garcia |
| 2004/0068235 A1 | | 4/2004 | Hallam |
| 2004/0068900 A1 | * | 4/2004 | Moran .................. G09F 3/00 40/311 |
| 2004/0089629 A1 | * | 5/2004 | Villaescusa ........ B65D 17/4012 215/388 |
| 2005/0039416 A1 | | 2/2005 | Hidding |
| 2005/0205513 A1 | | 9/2005 | Hidding |
| 2005/0220943 A1 | * | 10/2005 | Abrams .................. B65D 25/465 426/130 |
| 2005/0232813 A1 | * | 10/2005 | Karmali .................. A61B 5/150358 422/410 |
| 2006/0075651 A1 | | 4/2006 | Hamlet et al. |
| 2007/0077655 A1 | * | 4/2007 | Unger .................. G09F 23/00 435/404 |
| 2007/0235105 A1 | * | 10/2007 | Ramsey .................. A45F 3/16 141/323 |
| 2008/0302754 A1 | | 12/2008 | Lewin |
| 2008/0314933 A1 | | 12/2008 | Leonoff |
| 2009/0090688 A1 | | 4/2009 | Fruchter |
| 2010/0072099 A1 | * | 3/2010 | Klein .................. B65D 51/20 206/459.5 |
| 2010/0154800 A1 | * | 6/2010 | Chang .................. A61M 16/04 128/207.15 |
| 2010/0292800 A1 | * | 11/2010 | Zubok .................. A61F 2/4684 623/17.16 |
| 2011/0233236 A1 | | 9/2011 | Brown et al. |
| 2012/0138563 A1 | | 6/2012 | Brumfield |
| 2012/0248111 A1 | * | 10/2012 | Bear .................. C12M 27/12 220/212 |
| 2013/0125430 A1 | | 5/2013 | Whittemore et al. |
| 2014/0175133 A1 | * | 6/2014 | Metropulos .......... B67D 1/0802 222/400.7 |
| 2014/0299629 A1 | | 10/2014 | Al Kalloti et al. |
| 2016/0207045 A1 | | 7/2016 | Unger et al. |
| 2016/0215248 A1 | | 7/2016 | Keitel et al. |
| 2016/0296422 A1 | | 10/2016 | Brown |
| 2017/0007504 A1 | | 1/2017 | Brown et al. |
| 2017/0112308 A1 | | 4/2017 | Bennevendo et al. |
| 2018/0140119 A1 | * | 5/2018 | Shields .................. B65D 47/06 |
| 2018/0148231 A1 | * | 5/2018 | Pennington .......... B65D 41/045 |
| 2019/0021762 A1 | * | 1/2019 | Millis .................. A61J 15/0015 |

OTHER PUBLICATIONS

Sigma-Aldrich, Inc., Acrodisc® Syringe Filters, https://www.sigmaaldrich.com/catalog/product/aldrich/z260304?lang=en&region=US, printed May 4, 2018.

* cited by examiner

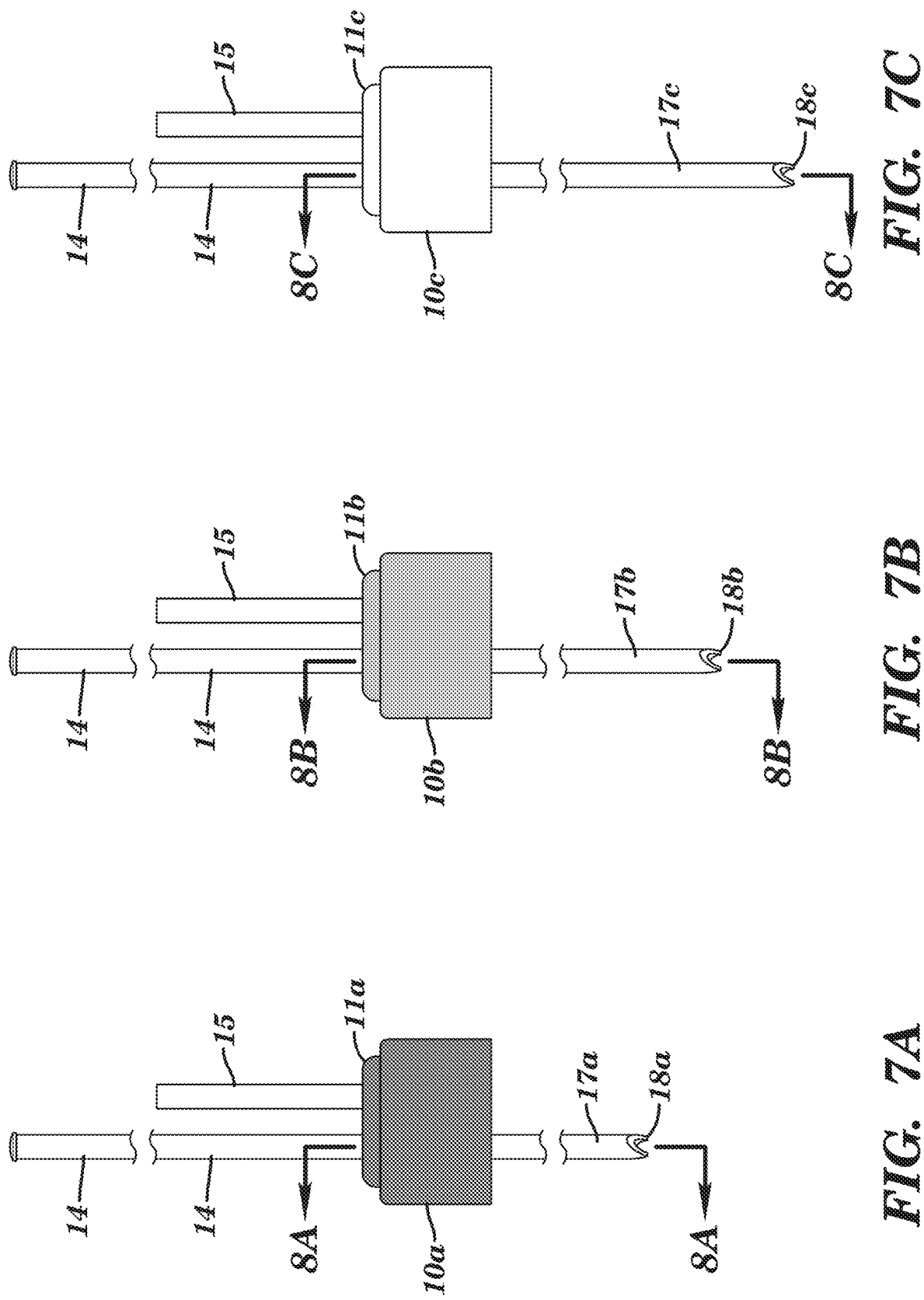

SYSTEM, APPARATUS AND METHOD FOR CODING CAPS FOR DIFFERENT BOTTLE SIZES

This application is a continuation of International Patent Application No. PCT/US2019/034761, with an international filing date of May 30, 2019, which claims priority to U.S. Provisional Patent Application No. 62/678,055, filed May 30, 2018, in which both such International and Provisional Applications are incorporated herein by reference.

FIELD OF THE INVENTION

The present invention relates to a system, apparatus, and method for coding caps for different bottle sizes, and in particular to, a system, apparatus, and method for coding caps for different bottle sizes where each cap has a tube fixed to a proper length to reach or extend along an interior bottom of a bottle when engaging the cap coded for the size of such bottle. In a preferred embodiment, at least a portion of each of the caps are visually coded by being one of multiple colors each associated with a different bottle size, but indicia along each of the caps may alternatively, or in addition to color, be used to visually code bottle size. The invention is useful in experiments using a sealed bioreactor container or vessel, typically having multiple tubes providing feeder lines to bottles of different sizes, to assure that the ends of the feeder lines reach the interior bottom of such bottles, so that if needed, fluidic medium therein can be withdrawn down to such bottom. The invention further provides a plurality of apparatuses which may be in the form of kits each having at least a tube providing a feeder line and a cap coded for use with a different size bottle.

BACKGROUND OF THE INVENTION

A bioreactor is a manufactured or engineered container or vessel that supports a biologically active environment. Biotech research facilities use bioreactors for conducting experiments. Often when setting up or operating a bioreactor, one or more lines are each provided by tubing attached to the bioreactors in order to add or remove a medium from the environment of the bioreactor. Different size bottles are used depending on the amount being collected from or dispersed into the bioreactor. It is important that bottle size be selected so that the right length of feeder line tubing reaches or just extends along the interior bottom of the bottle so that contents therein can be fully drawn via the feeder lines from the bottles for use in the experiment as needed. With multiple sized bottles being used with multiple feeder lines each via a cap onto the bottles, there has been no quick way for a lab technician, scientist or researcher to be sure that they are using the right additive feeder line for the intended bottle. While bottle sizes are easily deciphered by visual inspection, the selection of feeder line tubing for bottles are not. It would be desirable to provide a system which reduces errors in setting up additive feeder lines to avoid a bioreactor based experiment failing prematurely due to incompatible bottles being used due to feeder lines not reaching the bottom of such bottles. Further, it would be desirable to readily inspect an experiment with additive feeder lines to bottle size so that any errors can be corrected prior to running the experiment or can be quickly changed before the experiment prematurely fails.

SUMMARY OF THE INVENTION

Accordingly, it is a feature of the present invention to provide a system, apparatus, and method for coding caps with tubes which can provide feeder lines for different bottle sizes, so that such tubes will be of proper length to reach an interior bottom of bottles when engaging the caps coded for the size of such bottles in order to assure that fluidic medium content can be withdrawn to the bottom of the bottles.

It is a further feature of the present invention to provide a plurality of apparatuses each having at least a tube and a cap coded for use with one of different sizes of bottles, where such apparatuses may be provided to users as kits.

Briefly described, the system embodying the present invention comprises a plurality of caps having visual coding for use with different sizes of bottles at least in accordance with a height of the bottles from their closed bottom end to their opposing open end suitable for engaging each of the caps. Each of the caps comprises a tube mounted to, or through, the cap to extend a selected length which enables one end of the tube to reach or extend along an interior surface of the closed bottom end of any of the bottles of the height to which the cap is coded for use therewith when engaging the cap.

Preferably, the caps are each provided with a visual coding of color, along at least a portion of the cap, and/or indicia on a label along the cap, of one of a plurality of colors associating the cap for use with different sizes of bottles at least in accordance with a height of the bottles. When each of the caps are visually coded by color, the color may be in the plastic material forming the body of the cap, and/or in the material of the cap having an aperture for, and/or in the color of ink printed or coated upon an adhesively applied label to the cap. When each of the caps are visually coded by indicia, each of the caps has one of a plurality of different indicium preferably of one of the plurality of colors, but other indicium may be used to provide visual coding.

Each of the caps have at least one aperture, and means for fixing the tube to provide such selected length when extended through, or received in the aperture, in accordance with the visual coding of the cap. Such means provided may be mechanical locking element(s) along the interior of the aperture, such as barbed ring(s) or projection(s), a clamp or other member along exterior of the aperture that mechanically couples the tube to the cap, bonding material, e.g., liquid adhesive, applied along the interior of the aperture, frictionally engagement of the tube in the aperture, externally applied heat bonding the tube to the cap, such as by ultrasonic welding, or a combination thereof, to fix position of the tube with respect to the cap to retain its selected length.

Where such end of the tube receivable in a bottle represents a proximal end of such tube, the other or distal end of such tube extends away from the cap to a bioreactor container or vessel for communication of gas or fluid there through, enabling the tube to provide a feeder line to the bioreactor container or vessel through which contents of the bottle may transfer to the bioreactor, or be collected from the bioreactor in the bottle, as desired.

Alternatively, when the tube providing the selected length is mounted in an aperture of the cap, such tube is mounted into a lower end of such aperture, and another tube is mounted to an upper end of the aperture and extends away from the cap to a bioreactor container or vessel for communication of gas or fluid there through. Such another tube has one end either mounted into a port along the cap to such upper end of the aperture, or onto a port along the cap to such upper end of the aperture, such as by engaging barbs along the port's exterior to retain the tube to the cap.

Each of the caps further has an air vent through the cap provided by another aperture extending through a closed top end of the cap different from the one associated with the tube extended to a selected length from the cap. This another tube has a proximal end mounted to extend at least partially through such another aperture, and a distal end with an optional filtering device to filter air passing through the tube. Alternatively to using another tube, a port may be provided along the cap to such another aperture onto which such optional filtering device can be mounted.

The present invention further provides a method for coding caps for different bottle sizes comprising steps of: providing caps visually coded, such as by one or more of color or indicia, for use with different size bottles at least in accordance with height of the bottles; and mounting a tube to, or through, an aperture extending through each of said caps, to extend the tube to a length which enables one end of the tube to reach or extend along a bottom of any of the bottles of the height to which the cap is coded for when engaging the cap.

The mounting step further comprises a step of fixing the tube to extend the selected length when mounted to, or extended through, an aperture of each of the caps which enables one end of the tube to reach or extend along a bottom of any of the bottles of the height to which the cap is coded for when engaging the cap. In operation, each one of the caps engages onto an open end of one of the bottles having at least the height to which such cap is visually coded for.

The present invention also provides an apparatus having at least one tube having proximal and distal ends, and a cap having at least one aperture, extending through a closed top end of the cap, which is sized to receive the tube. Such tube is mounted to, or through, the aperture to extend a length from the cap to its proximal end. The cap is visually coded with one of a plurality of colors and/or indicia associated with bottles having one of a plurality of different sizes. The length of the tube from the cap to its proximal end is selected to enable such proximal end to reach or extend along an interior along the bottom end of any of the bottles of such one of the plurality of different sizes to which the cap is visually coded for. The cap may have another aperture through the closed top end of the cap to provide an air vent, which either extends to a port along the cap, or sized to receive a proximal one an additional tube where the distal end of the additional tube extends away from the bottle when engaging the cap. The distal end of the port or such additional tube may further have an optional air filtering device mounted thereupon.

The apparatus may represent a kit in a package or carton containing at least the cap, the tube mounted in or through the aperture to its fixed position with respect to the cap, and may further enclose items, such as the additional tube and an optional air filtering device mountable thereupon. In the case where the tube is mounted in a lower end of the aperture of the cap for extension to the selected length, a further tube may be provided in the kit mounted in the same aperture, but from the upper end thereof. The apparatus represents one of a multiple different apparatuses or kits, where each has one of the caps visually coded with a different one of the plurality of colors and/or indicia associated with bottles of different bottle sizes at least in terms of bottle height.

Optionally, one or more of the bottles each has a matching visual coding, such as along at least a portion of the bottle, as with those caps which are coded for use therewith. In the case where at least a portion of the caps and/or indicia have one of a plurality of different colors to provide the visual coding for the cap, bottles may each have an adhesively applied label, or the material forming all or a portion of the bottles, may provide the same or similar color matching the visual coding color of those ones of the caps which are coded for use with such bottles.

Preferably, each of the tubes in the above-described system, method and apparatus are flexible and can thus bend or flex about their lengths. To account for such flexibility, the selected length of the tube, when mounted to, or extended through, each cap is the same as the height of one of the bottles to which the cap is visually coded for plus preferably an additional tolerance (or offset) to assure that the end of the tube will reach or just extend along the interior bottom of such bottles when engaging the cap even with any bend or flexure of the tube. The tolerance is selected, in addition to enabling the end of the tube to reach or extend along the interior bottom of bottles despite any flexure(s), is limited in range to avoid the tube being too long that it could undesirably cause the end of the tube to bend or flex away from the interior bottom of the bottle, thereby making it difficult to fully withdraw contents all the way to the bottom of the bottle.

By selection of caps coded to bottles sized for such caps, tubes providing feeder lines automatically reach or extend along the bottoms of such bottles thereby improving experimental setup and operation by reducing human error in potentially using a missized bottle for a feeder line, and further readily enables visual verification of experimental setup.

BRIEF DESCRIPTION OF THE DRAWINGS

The foregoing and other features and advantages of the invention will become more apparent from a reading of the following description in connection with the accompanying drawings in which:

FIGS. 7A, 7B, and 7C are side views of an example of three different apparatuses in the system of the present invention, where each apparatus has a cap with a different length tube locked or fixed to the cap, where the caps are visually coded for different sized bottles by a different color so that such tubes is of a length that will reach or extend along the interior bottom of such bottles when engaged to the caps;

DETAILED DESCRIPTION OF THE INVENTION

Figure 1:
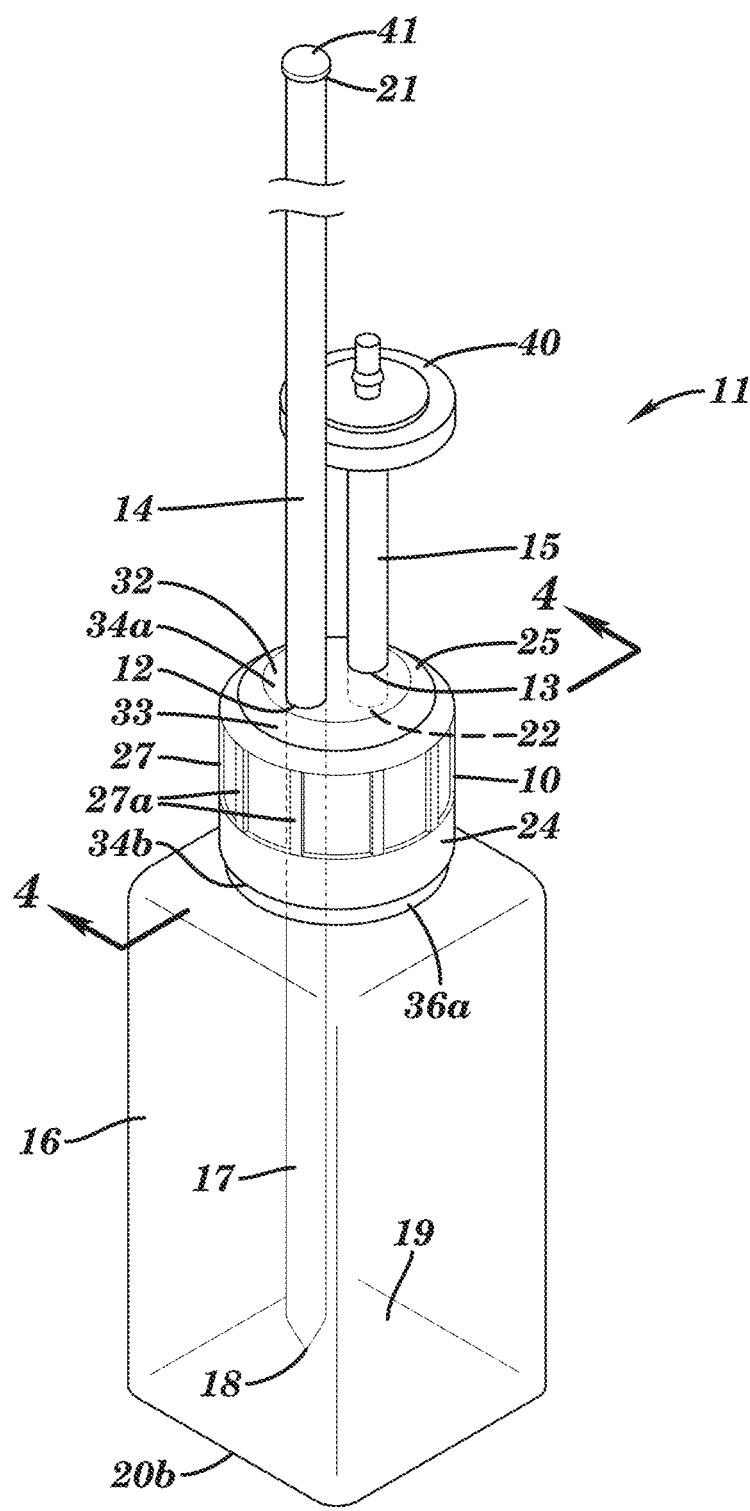
FIG. 1 is a perspective view of one of the apparatuses of the present invention having a cap with extending tubes, where the apparatus is shown engaged to an example bottle.
Figure 2:
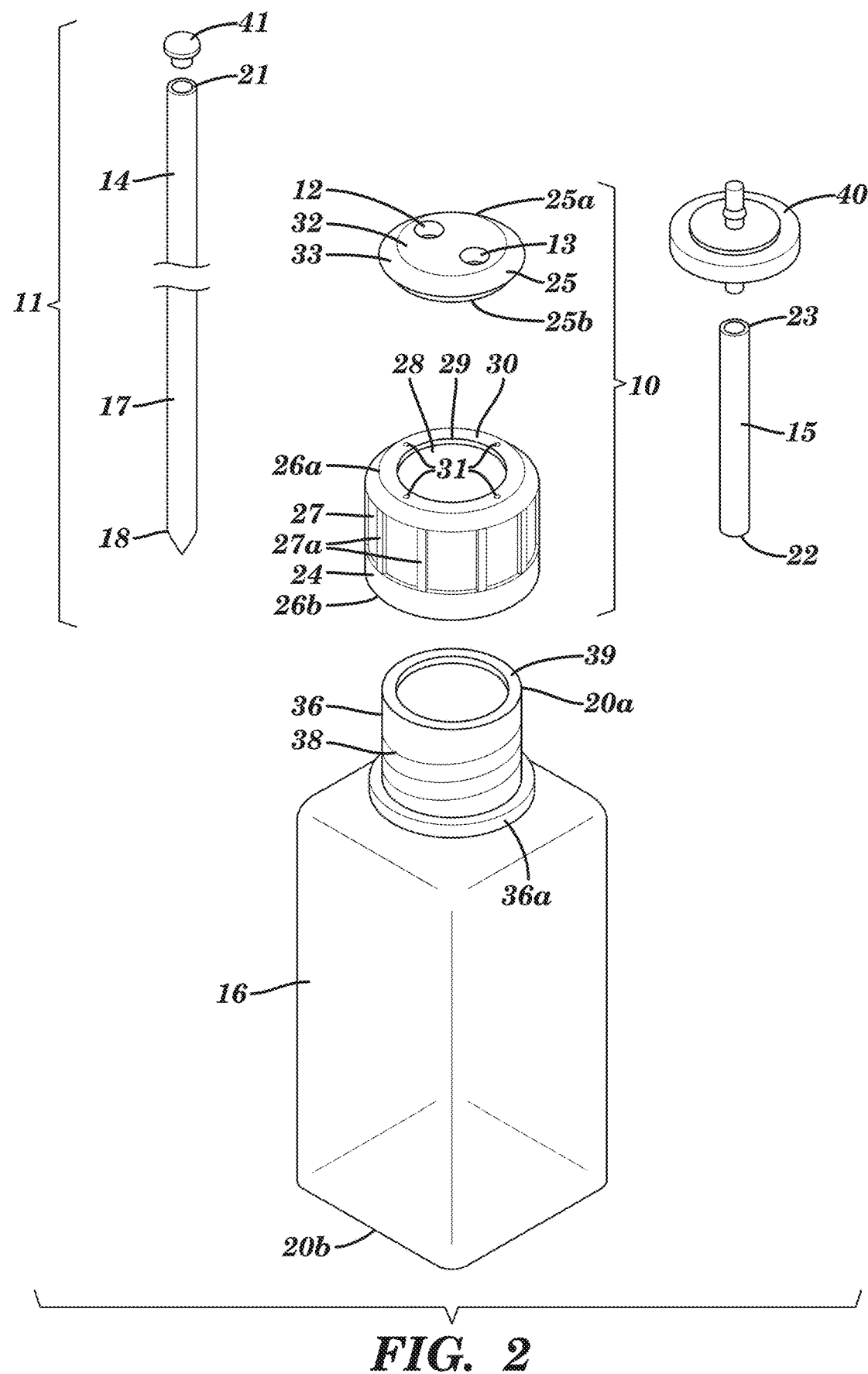
FIG. 2 is an exploded view of the apparatus of FIG. 1 and the example bottle.
Figure 3:
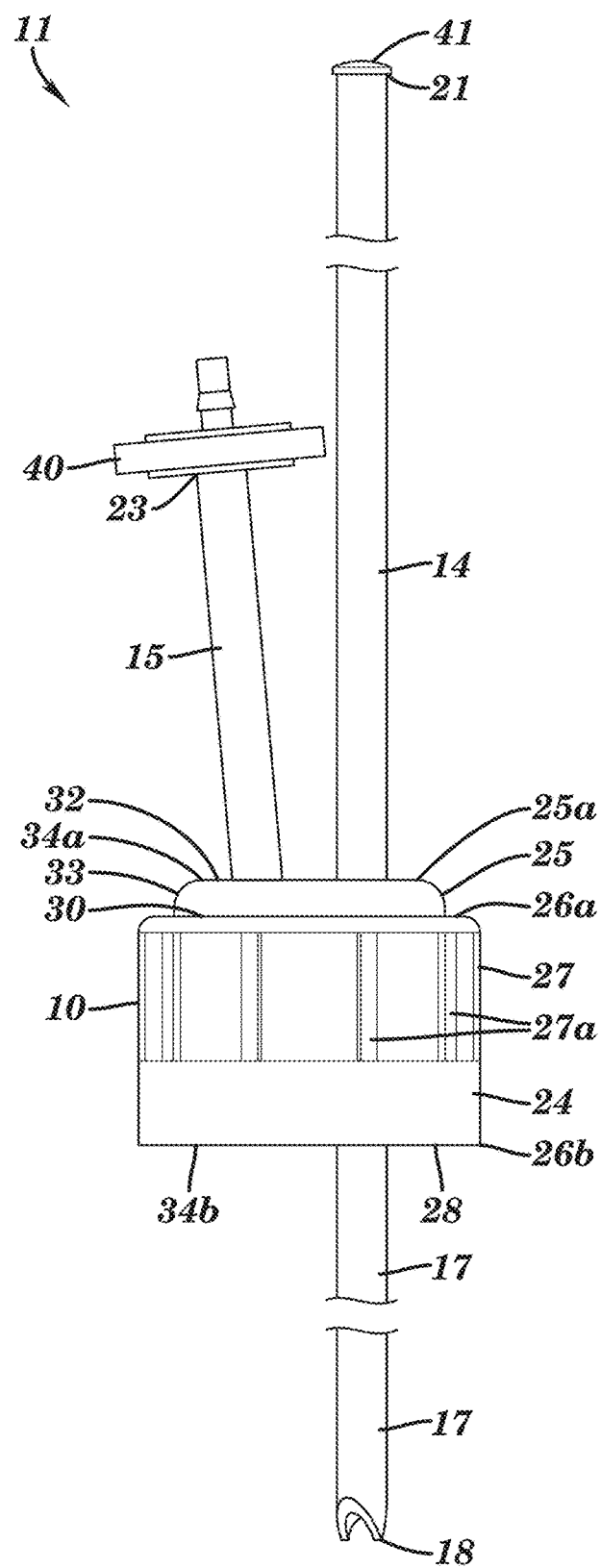
FIG. 3 is a side view of the apparatus of FIG. 1 removed from the example bottle.
Figure 4A:
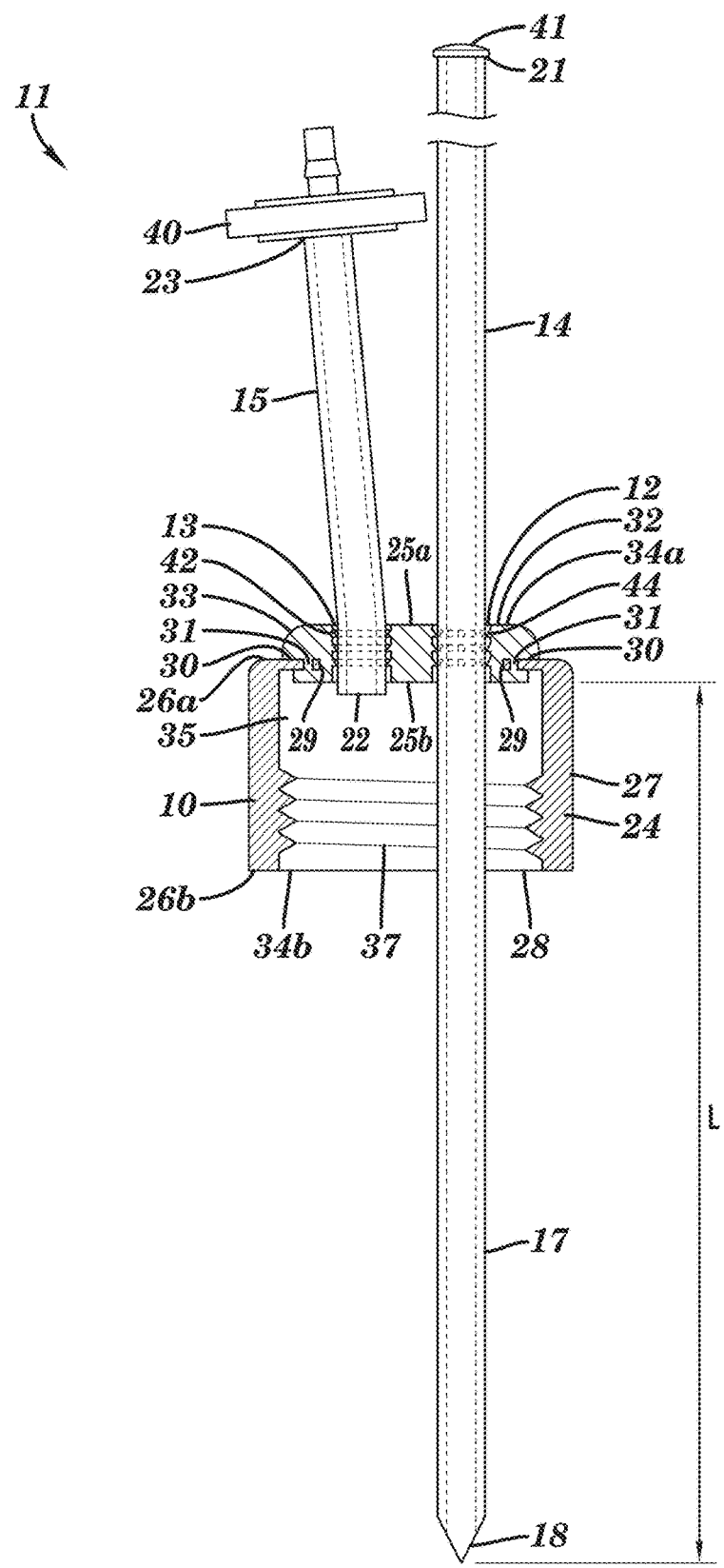
FIG. 4A is a cross-sectional view of the apparatus of FIG. 1 along line 4-4 in direction of arrows as the ends of such line with the bottle removed.
Figure 4B:
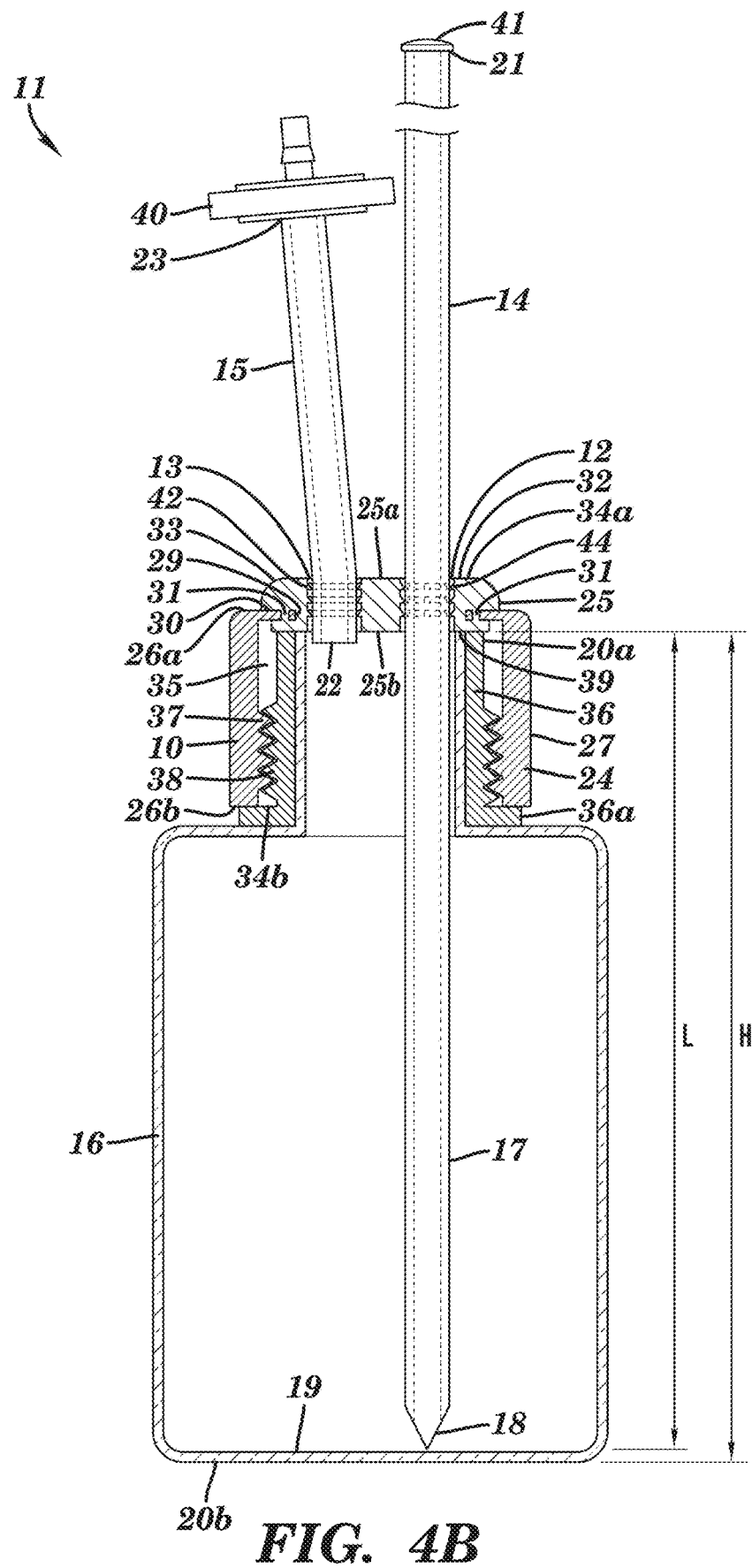
FIG. 4B is a cross-sectional view of the apparatus of FIG. 1 along line 4-4 in direction of arrows as the ends of such line showing the example bottle of FIG. 1 engaged to the apparatus.

Referring to FIGS. 1, 2, 3, 4A, and 4B, a cap 10 is shown having two apertures 12 and 13 which receive two tubes 14 and 15, respectively, to provide one of apparatuses 11 attachable to a bottle 16. Tube 14 extends through aperture 12 to a proximal end 18 and is mounted in a fixed position with respect to cap 10 so that tube 14 has a portion 17 thereof which extends to end 18. Portion 17 of tube 14 is of a fixed length L (FIGS. 4A and 4B) from aperture 12 to end 18 so that such end 18 will reach the interior surface 19 of a closed bottom end 20b of bottle 16 when cap 10 engages onto a top end 20a of bottle 16. The other tube 15 has a proximal end 22 mounted in aperture 13 of cap 10, and a distal end 23 with an optional air filtering device 40 mounted thereto. The distal end 21 of tube 14 extends from cap 10 and may of a variable length as desired by the user for attachment as a typical feeder line tubing to a bioreactor vessel (not shown) so that apparatus 11 enables communication of gas and/or fluid there through to or from the bottle 16 upon which the apparatus 11 is engaged. To facilitate communication of fluid, tube 15 is mounted to cap 10 in apparatus 11 to provide an air vent. An example of one of bottles 16 engaged to apparatus 11 is shown in FIGS. 1 and 4B when portion 17 of tube 14 is of a proper length selected for the bottle 16. FIGS. 3 and 4A show the assembled apparatus 11 prior to attachment to bottle 16. The example bottle 16 shown in FIGS. 1 and 4A need not be considered part of apparatus 11.

As caps 10 with different length portions 17 of their tube 14 are needed to engage bottles 16 of different sizes, at least in terms of the height dimension H (FIG. 4B) of the bottle 16 between its top end 20a and opposing bottom end 20b, the present invention provides a system of multiple caps 10 visually coded for associated use with different bottle sizes where each differently coded cap 10 has a portion 17 of tube 14 extending therefrom of a length selected in accordance with the bottle 16 of the proper size, at least in height, coded for that cap. This enables users, such as laboratory technicians, scientists or researchers, in experiments using a bioreactor vessel (device or container) to easily visually associate the proper cap 10 by its visual coding for the particular size of bottle 16 such that the portion 17 of tube 14 from the cap 10 will be of a length enabling fluidic contents of the bottle to be withdrawn all the way to the bottom 20b of the bottle 16, if needed. Preferably, caps 10 are coded by visually presenting on at least a portion of the cap one of multiple different colors each associated with a different bottle size, indicia may in addition, or alternatively, be provided to similarly code by bottle size. Examples of different ones of apparatus 11 in the system of caps so visually coded for different sizes of bottles are shown in FIGS. 7A-C, 8A-C, and 9, as will be described later.

Filtering device 40 is connected to tube 15 by frictionally engagement into end 23, which extend away from cap 10 and the bottle 16 when engaged to such cap. Filtering device 40 has an internal screen or membrane to prevent undesirable material, such as particulates, from entering tube 15 and thus into the bottle 16 when attached to cap 10. For example, filtering device 40 may be Whatman Puradisc 25 mm diameter syringe filter with a Polytetrafluoroethylene (PTFE) membrane having a 0.2 micrometer pore size, available from GE Healthcare, model number 6785-2502, or a 25 mm syringe filter with a PVDF membrane, such as manufactured by Pall Corporation of Port Washington, N.Y., U.S.A., but other air filtering devices may be used with different sized openings or pores, and otherwise mechanically coupled to tube 15. Also, an optional protective plug 41 may be inserted into end 21 of tube 14. Such plug 41 is removed prior to attachment of tube 14 for communication with a bioreactor vessel (not shown). The end 18 of tube 14 is preferably cut to a triangular shape, rather than square cut, to avoid risk of its abutment to surface 19 along bottom 20b inadvertently closing tube 14. Tubes 14 and 15 may each be of flexible tubing, such as thermoplastic polyurethane (TPU) material, but other tube material may be used. As illustrated in FIGS. 1, 4A, and 4B, where tube 14 extends through aperture 11 to the fixed length for its coded cap 10, tube 14 has a circular cross-section which is maintained through the aperture at least until opening at end 18 with the preferably triangular (non-square) tip.

Cap 10 is composed of a cylindrical body 24 with an insert molded portion 25 providing apertures 12 and 13. Cylindrical body 24 is of rigid plastic material, such as molded polypropylene, polycarbonate, or other polymer, shaped to form a cap or cover that can close over open top end 20a of bottle 16 (FIGS. 2 and 4B). As best shown in FIGS. 4A and 4B, body 24 has a upper end 26a and a lower end 26b, with a generally cylindrical wall 27 and a central opening 28 extending between ends 26a and 26b. Along opening 28 at upper end 26, wall 27 inwardly extends to provide an annular flange or lip 30 which reduces the diameter of opening 28 at upper end 26a about a circular edge 29. Vertical ridges 27a may be provided along the outer surface of cylindrical wall 27 to assist a user in manually turning cap 10 when engaging upon (or disengaging from)

a bottle 16. In the case where different colors are used to code caps for different size bottles 16, preferably different cylindrical bodies 24 are molded which are the same, but for being of plastic material of one of the different colors.

Elastomeric material is insert molded onto cylindrical body 24 to form portion 25 and overmolds along annular lip 30 so that part of the material extends below annular lip 30 while the rest extends there above along upper end 26a of cylindrical body 24. Cylindrical body 24 has small holes 31 spaced along annular lip 30 so that when over molding body 24 the material forming member 25 flows through holes 31 to assist in mechanically locking portion 25 in a fixed position onto body 24 in the completed cap 10. The elastomeric material of portion 25 is a polymer (or rubber) having for example a durometer (hardness) of 70A, but other durometer material may be used as desired. While portion 25 closes the top end 26a of body 24, along portion 25, between its top 25a and bottom 25b, apertures 12 and 13 are formed coaxial with each other having a longitudinal dimension parallel to the height of cylindrical body 24 between its ends 26a and 26b. Tubes 14 and 15 having an outer diameter, such as for example 0.25 inches, which is slightly more than the diameter of apertures 12 and 13 so that material of portion 25 along the interior of apertures 12 and 13 can deform in response to receiving tubes 14 and 15, respectively, to enable their sealing engagement in cap 10 along portion 25. Other diameter tubes 14 and 15 may be used, which may be the same of different from each other, and having apertures 12 and 13 sized in diameter for enable sealing engagement therewith. Portion 25 of cap 10 above annular lip 30 provides the top 34a of cap 10 with a level central circular surface 32 through which apertures 12 and 13 extend, and a beveled outer circular surface 33, but other shape than beveled may be used such as square. For purposes of illustration, the insert molded portion 25 of cap 10 is shown removed from cylindrical body 24 in the exploded view of FIG. 2.

As shown in FIGS. 4A and 4B, cap 10 has an interior cavity 35 provided by central opening 28 in cylindrical body 24 extending from insert molded portion 25 at top 34a of cap 10 to an open bottom 34b of cap 10 provided by bottom 26b of cylindrical body 24. Cylindrical body 24 of cap 10 is dimensioned so that a cylindrical extension 36 at the open top end 20a of a bottle 16 that can be received in cavity 35 of cap 10 via its open bottom 34b. When so received, threads 37 along the interior surface of wall 27 of cap 10 engage exterior threads 38 along cylindrical extension 36, as best shown in FIG. 4B, such that turning the bottle 16 and cap 10 with respect to each other tightens the cap upon the bottle, thus enabling engagement of cap 10 to bottle 16. The elastomeric material of portion 25 of cap 10 under annular lip 30 may then provide a gasket enabling cap 10 to sealingly engage against the bottle 16 along a top edge 39 thereof. Thus, cap 10 can sealingly engage bottle 16 while providing tubes 14 and 15 in communication with the interior of the bottle when the cap closes the open top end 20a of the bottle as shown for example in FIG. 4B. An optional collar 36a at the base of cylindrical extension 36 may align to face the bottom 34b of cap 10 when engaged upon bottle 16.

Figure 6A:
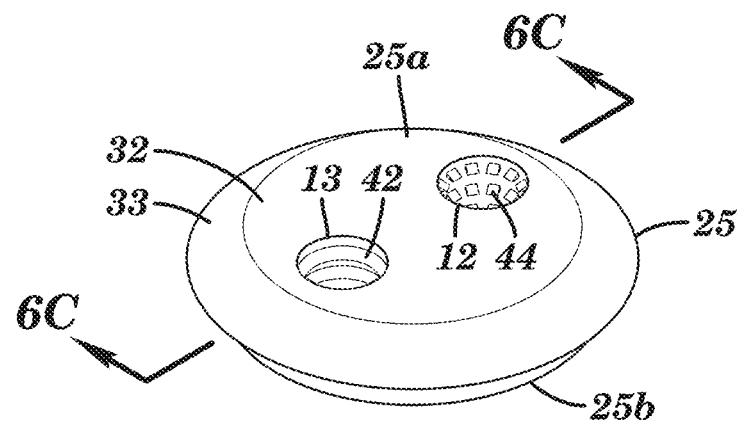
FIGS. 6A and 6B are perspective and top views, respectively, of an insert molded portion of the cap of the apparatus of FIGS. 1, 2, 3, 4A, and 4B, such insert molded portion being shown without tubes and removed from the cylindrical body of the cap in order to illustrate tube position locking elements along apertures of the cap for the tubes.
Figure 6B:
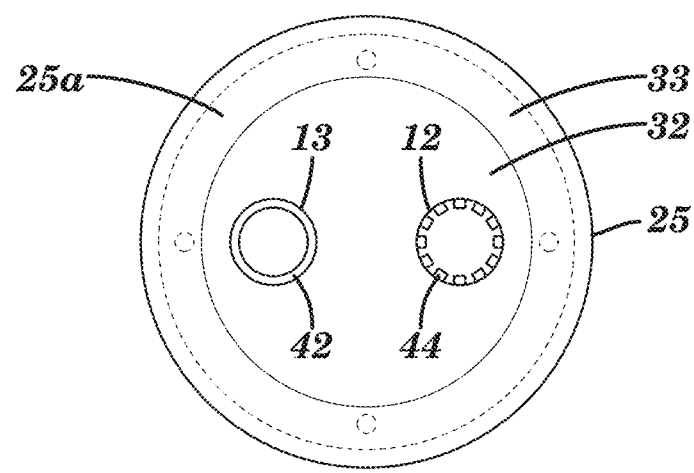
Figure 6C:
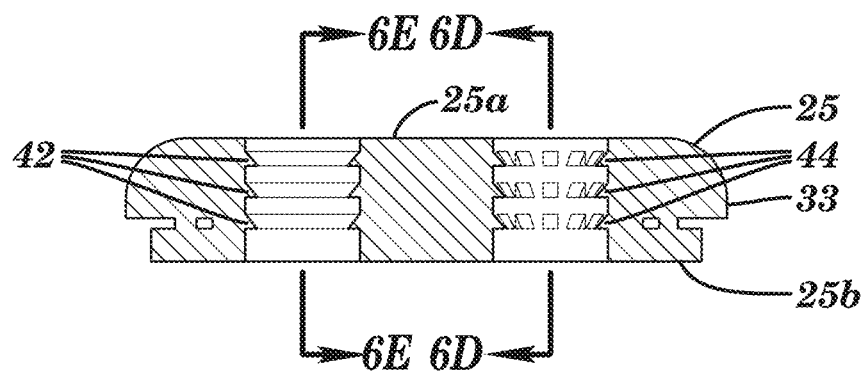
FIG. 6C is a cross-sectional view of the insert molded cap portion of FIG. 6A along line 6C-6C in direction of arrows as the ends of such line.
Figure 6D:
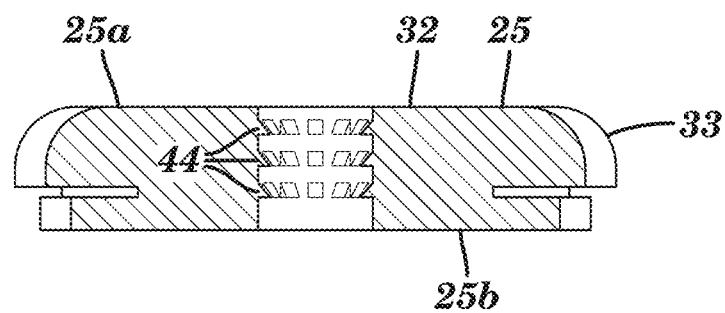
FIG. 6D is a cross-sectional view of the insert molded cap portion of FIG. 6C along line 6D-6D in direction of arrows as the ends of such line.
Figure 6E:
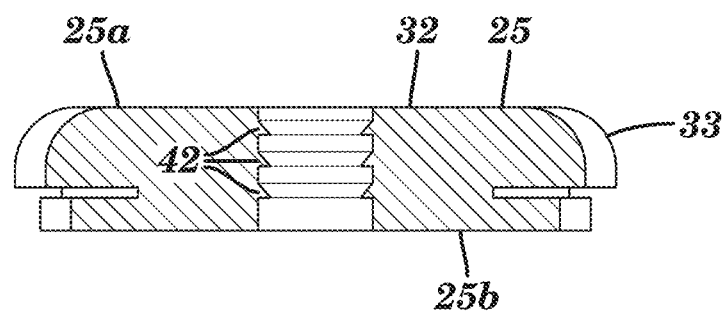
FIG. 6E is a cross-sectional view of the insert molded cap portion of FIG. 6C along line 6E-6E in direction of arrows as the ends of such line.
Figure 8C:
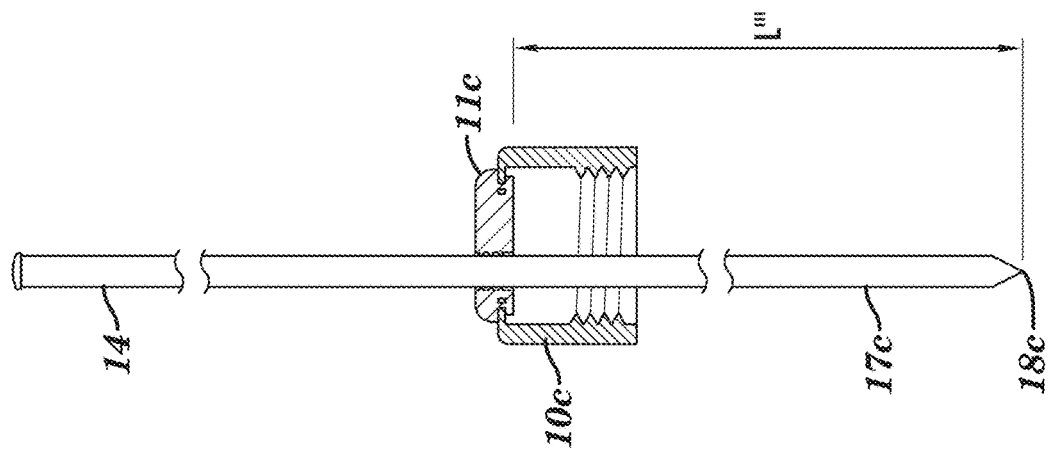
FIGS. 8A, 8B, and 8C are cross-sectional views of FIGS. 7A, 7B, and 7C, respectively, along lines 8A-8A, 8B-8B, 8C-8C, respectively, in direction of arrows at the ends of such lines.
Figure 8B:
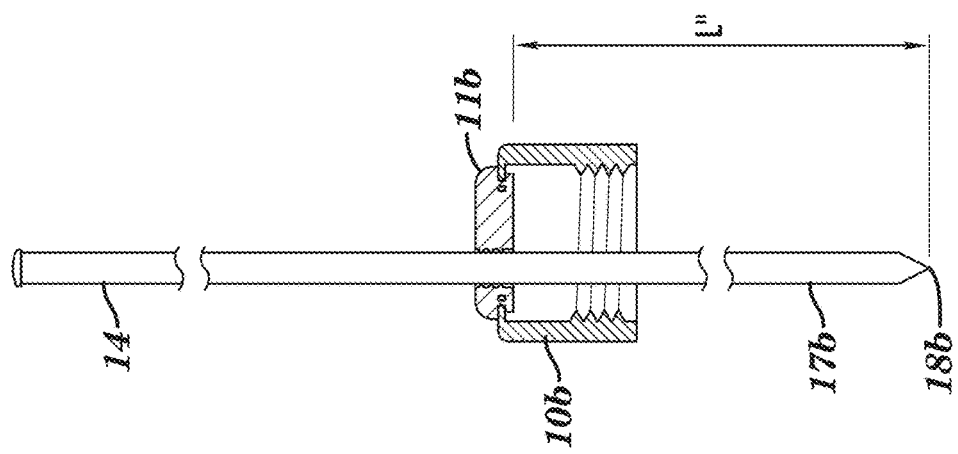
Figure 8A:
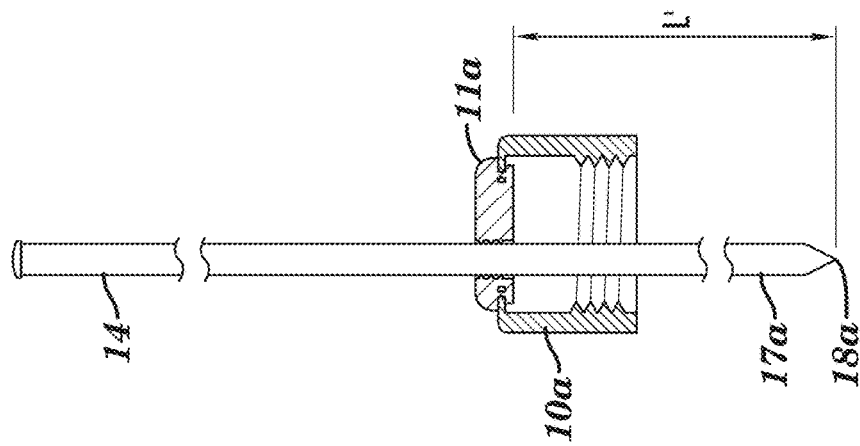

Referring to FIGS. 6A, 6B, 6C, 6D, and 6E, one or more mechanical locking elements are provided to mechanically fix the position of tube 14 with respect to aperture 12 of cap 10 to retain portion 17 of tube 14 at its selected length, as described earlier. The cap's insert molded portion 25 is shown removed from the cap in FIGS. 6A, 6B, 6C, 6D, and 6E, where dashed lines in FIG. 6B show where cylindrical body 25 was overmolded. Mechanical locking elements may be barbs in the form of barbed rings 42 or a ring of barbed projections 44 extending radially inward from the interior surface of aperture 12. Preferably, multiple barbed rings 42 or rings of barbed projections 44 are provided along aperture 12 between ends 25a and 25b, as shown in FIGS. 6A, 6B, 6C, 6D, and 6E (and in cross-sectional views of FIGS. 4A and 4B), but a single barbed ring 42 or single ring of barbed projections 44 may be used in aperture 12. For purposes of illustration, barbed projections 44 are shown in aperture 12, and multiple barbed rings 42 are shown in aperture 13 for fixing position of tubes 14 and 15, respectively, however the same or different form of such mechanical locking elements may be used in both apertures 12 and 13. The barbed rings 42 or projections 44 as best shown in FIGS. 6E and 6D, respectively, may each have a right triangle shape. Cross-sectionally in a direction along the aperture's radius, each ring 42 or projection 44 has two surfaces extending from the wall of aperture 12 or 13, one surface facing end 25a and the other surface facing end 25b. The surface facing end 25a represents the hypotenuse of a right angle made by the surface facing 25b with the longitudinal dimension of the wall of the aperture, such that the two surfaces converge distally from the wall to form a barbed ring or projection. However barbed rings or projections may have other cross-sectional shapes.

After extending tubes 14 and 15 in respective apertures 12 and 13 as described earlier, external pressure from mechanically locking elements 42 or 44 (FIGS. 4A, 4B, 6A, 6B, 6C, 6D, and 6E) therein bears against the outer surfaces of the tubes thereby mounting them in a fixed position in the respective apertures (FIG. 4B). Such mechanically locking elements 42 or 44 may be formed when portion 25 is insert molded onto cylindrical body 24 of cap 10, and thus are of the same material as portion 25. Preferably, barbed rings 42 or projections 44 when present allow tube 14 or 15 to be inserted and pulled/pushed through aperture 12 or 13, respectively, from end 25a in a direction toward end 25b through cavity 35 of cap 10 due to downward angle of each barbed ring or projection surface facing end 25a with respect to the aperture wall, but such same rings or projections resist passage of such tube in the opposite direction where they then lock (or at least resist movement) fixing the tube in its aperture of cap 10.

Figure 5A:
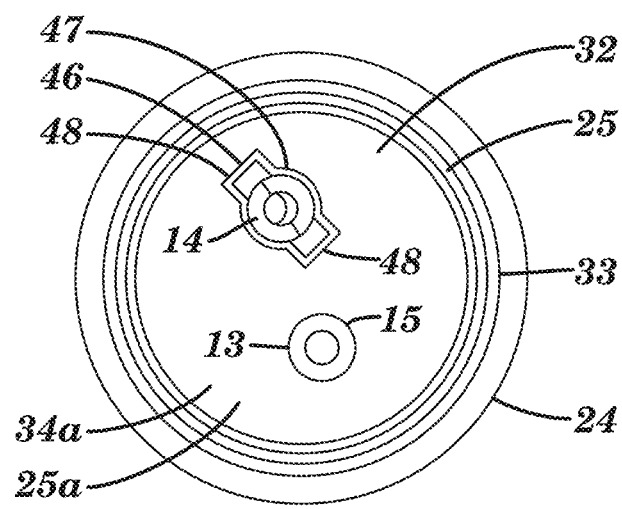
FIG. 5A is a top view of the apparatus of FIG. 3 having an optional clamp for mechanically locking or fixing the position of one of the tubes with respect to the cap of the apparatus.
Figure 5B:
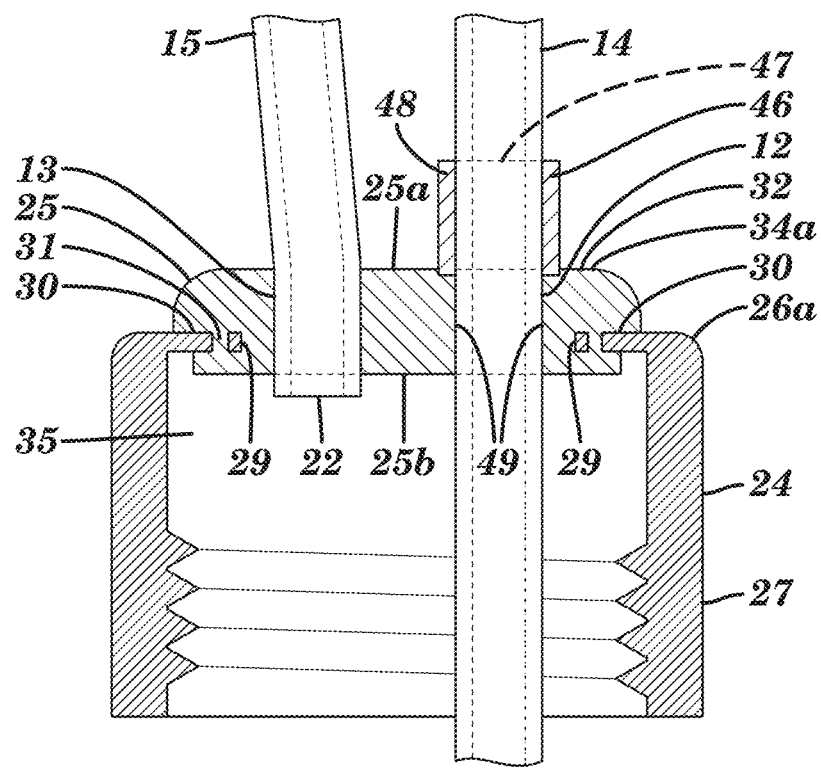
FIG. 5B is a partial broken view of FIG. 4A along the cap of the apparatus in which the locking members of FIG. 4A are removed from the apertures of the cap that receive tubes, and the optional clamp of FIG. 5A and optional bonding material are shown for locking or fixing position of one of the tubes to one of the apertures.

Alternatively, or in addition if needed, other mechanical locking or fixing elements may be used, such as a clamp 46 shown in FIGS. 5A and 5B. Clamp 46 is a stainless steel loop 47 having two ends 48 wrapped about tube 14 along top 34a of cap 10 so that as steel loop 47 is crimped about tube 14, it also grips into material of portion 25 of along top 34a. While tube 14 extends to a selected length and then so mechanically locked to mount tube 14 to cap 10 by element 42, 44, or 46 in accordance with the visual coding, e.g., color and/or indicia code, associated with the cap 10 which receives tube 14, tube 15 can be extended through aperture 13 as shown in FIG. 4A or partially through the aperture 13 with or without mechanical locking element(s).

Non-mechanical locking or fixing elements may be used instead of, or in addition to, mechanical locking elements 42, 44, or 46, in the form of liquid adhesive (or other bonding material) 49 (FIG. 5B) which when cured locks the position tube 14 with respect to aperture 12 of cap 10. Such liquid adhesive may be placed along the top and/or bottom of portion 25 of cap 10 around the exterior surface of the tube extended in aperture 12. Preferably, the adhesive can bind to materials forming both portion 25 and the tubes. Tube 15 may be similarly locking in position in aperture 13 if desired. As described earlier, apertures 12 and 13 of cap 10 are of a diameter to enable their associated tubes 14 and 15 to seal about the surfaces of cap 10 which abut around tubes 14 and 15. The use of liquid adhesive in one or both apertures 12 and 13 can better assure such seal along one or both tubes 14 and 15, respectively. Other non-mechanical locking or fixing without elements 42, 44, or 46 are shown in FIGS. 5C, 5D, and 5E.

Figure 5C:
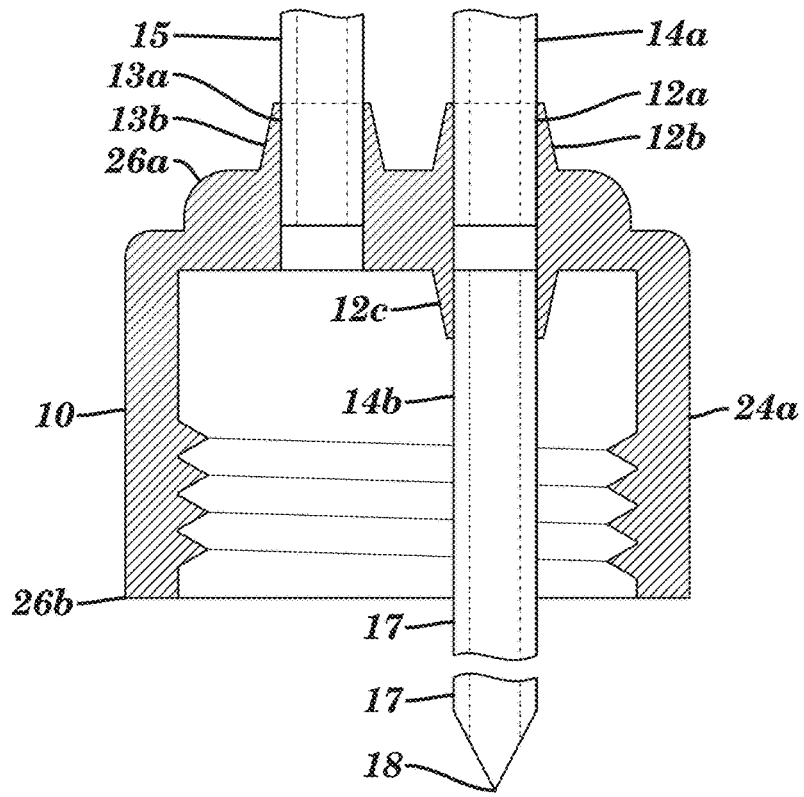
FIG. 5C is a partial broken cross-sectional view similar to FIG. 4A showing another embodiment of the cap of the apparatus of FIG. 1.

Referring to FIG. 5C, another embodiment of cap 10 is shown in which the cap is composed of a generally cylindrical body 24a with open bottom end 26b, and closed top end 26a but for two apertures 12a and 13a that extend there through. Each of apertures 12a and 13a has an upper end that extends through ports 12b and 13b, respectively, which extend upward along the topside of end 26a of cap 10. Tubes 14a and 15 are received into apertures 12a and 13a, respectively, via ports 12b and 13b, respectively. Apertures 12a has a lower end that extends through a port 12c along the cap 10 disposed opposite port 12b along the underside of end 26a. One of two ends of a tube 14b is received in aperture 12a into port 12c via open end 26b so that the other of such ends of tube 14b provides end 18 of portion 17 as described above. The diameter of apertures 12a and 13a at ports 12b, 12c, and 13c, respectively, are each slightly smaller than the outer diameter of tubes 14a, 14b, and 15, respectively, so that the respective end of such tubes 14a, 14b, and 15 frictionally engage when pushed into ports 12b, 12c, and 13c to mount or fix the tubes to cap 10. In this case, tube 14 as described earlier is provided by two tubes 14a and 14b, and if those tubes are not in abutment in aperture 12a, further provided by such portion of aperture 12a between tubes 14a and 14b, so that so that tubes 14a and 14b are in communication with each other via aperture 12a to enable passage of gas or fluids there through to or from bottle 16 when engaging cap 10. The body 24a forming the cap 10 and its apertures 12a and 12b, and ports 12b, 12c, and 13b, may be of the same rigid plastic material as described for body 24 without need for elastomeric portion 25. The cap 10 of FIG. 5C operates in the same manner as described above, but where portion 17 of tube 14 is represented by tube 14b being positionally fixed to extend partially through aperture 12a when mounted by frictionally engagement in port 12c of the cap, and tube 14b is same, or approximately the same, selected length L from the cap's top end 26a to end 18 as shown in FIGS. 4A and 4B in accordance with the visually coding of cap 10. Tube 14a may extend away from the cap 10 to a bioreactor container or vessel (not shown) in the same manner as tube 14.

Figure 5D:
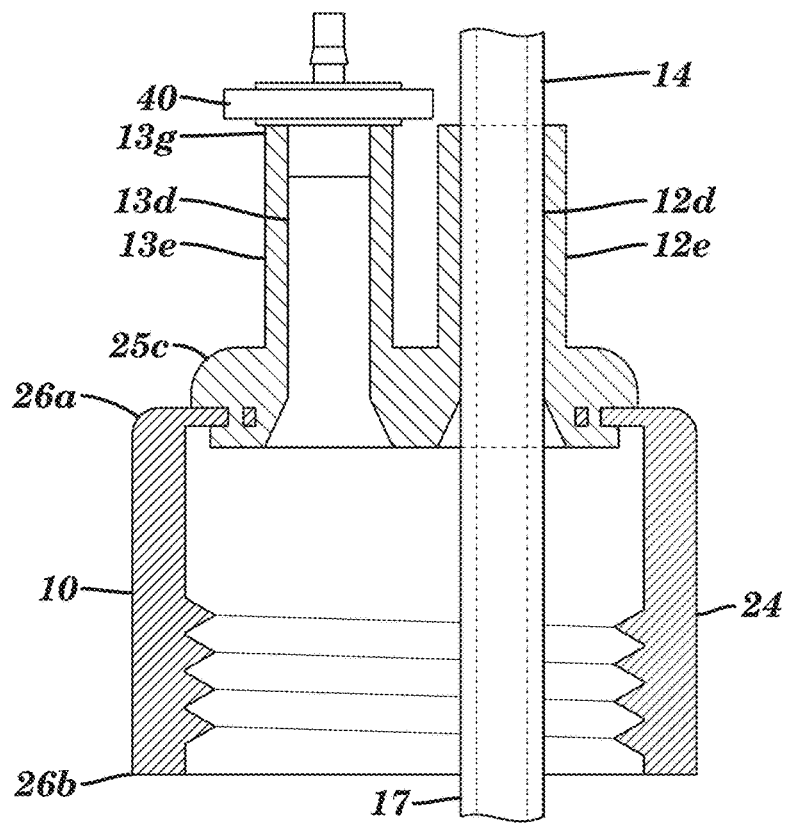
FIG. 5D is a partial broken cross-sectional view similar to FIG. 4A showing a further embodiment of the cap of the apparatus of FIG. 1.

Referring to FIG. 5D, a further embodiment of cap 10 is shown in which a portion 25c of cap 10 provides apertures 12d and 13d that extend along the upper end 26a of the cap. Each of apertures 12d and 13d has an upper end that extends through ports 12e and 13e, respectively, which extend upward along the topside of end 26a of cap 10. Tube 14 extends through aperture 12d, via port 12e, by having the diameter of aperture 12d slightly smaller than the outer diameter of tube 15. Port 13e provides an air vent through aperture 13d, and optional filter device 40, as described earlier, may be mounted in upper open end 13g of aperture 13d to filter air, and thus tube 15 is not needed. Ports 12e provides an extended portion of cap 10 for enabling application of heat thereto to weld or bond portion 25c material at ports 12e or tube 14, where such positionally fixes tube 14 after portion 17 of tube 14 is extended to its selected length L in accordance with the visually coding of cap 10. Such heat may be provided by an ultrasonic welder or other externally applied heating mechanism. Portion 25c may be formed in the same manner as portion 25 described earlier and of the same material, but with the extensions provided by ports 12e and 12f. However, other material may be used to form portion 25c which enables by applied heat thereto to weld or bond portion 25c at least a portion of the material along port 12e to tube 14 to mount or fix tube 14 to cap 10.

Figure 5E:
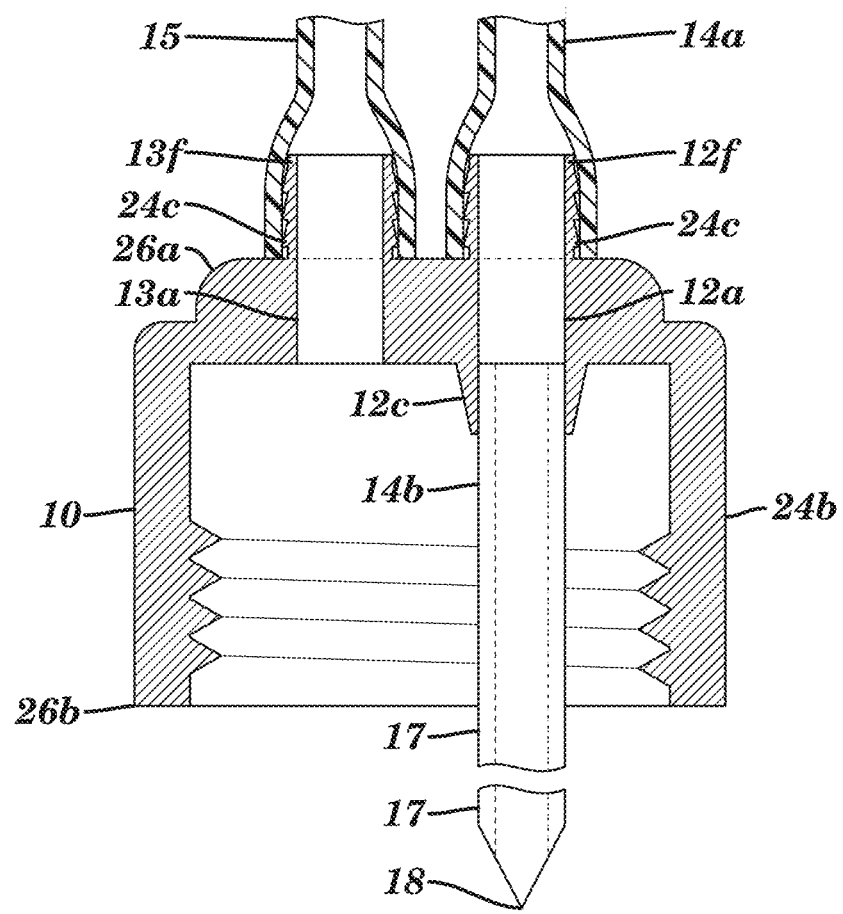
FIG. 5E is a partial broken cross-sectional view similar to FIG. 4A showing a still further embodiment of the cap of the apparatus of FIG. 1.

Referring to FIG. 5E, a still further embodiment of cap 10 is shown in which the cap is composed of a body 24b with two apertures 12a and 13a that extend through the closed top end 26a of the cap similar to the cap of FIG. 5C. Each of apertures 12a and 13a has an upper end that extends through ports 12f and 13f, respectively, which extend upward along the topside of end 26a of cap 10. Concentric barbs 24c are provided along the outer diameter of each of ports 12f and 13f. Each of tubes 14a and 15 are pushed over upon their respective port 12f and 13f so that the barbs 24c engage the interior of the tube to retains the tube to the port, and thus to cap 10. Other than the engagement of tubes 14a and 15, other elements of cap 10 are the same as described in connection with FIG. 5C, where port 12c is provided along the underside of end 26a of the cap opposite port 12f for retaining tube 14b therein, and the communication of tubes 14a and 14b via aperture 12a. Optionally, a heat shrinkable sleeve may be placed around each of tubes 14a and/or 15 when engaged upon ports 12f and/or 13f, respectively, so that with applied heat to the material of the sleeve shrinks to further lock the tube to its port.

The apparatus 11 may be provided in a kit having a cap 10 with a tube 14 (or tube 14b of FIGS. 5C and 5E) mechanically and/or non-mechanically locked thereto, as described above, to a fixed length along portion 17 for the particular visual coding, e.g., color and/or indicia code, for the cap. Other than the cap 10 being pre-assembled with tube 14, the other components of the kit, such as tube 15, and optional filtering device 40 and plug 41, may be provided as separate elements in the kit so that the user can complete assembly of apparatus 11 before or after engagement of cap 10 of the kit to a desired bottle 16. The kit is provided in a package or carton for assembly of apparatus 11. Optionally, tube 15 (or tube 14a of FIGS. 5C and 5E) may be pre-mounted to the cap 10 in the kit, as described earlier. The filtering device 40 and plug 41 may be pre-mounted to their respective tubes as well. In the case of FIG. 5D, tube 15 is not needed and filtering device 40 may be pre-mounted at end 13g of port 13d in the kit. Each kit preferably is for use with a particular size of bottles 16 coded for the cap 10 of the kit, and different kits may be provided each with apparatus 11 with a different one of cap 10 visually coded for a different bottle size. Thus caps 10 in each of the kit are identical, except for the being visually coded for different size bottles in accordance with the selected length of mounted tube 14 (or 14b of FIGS. 5C and 5E) locked (positionally fixed) to the cap 10 along its aperture 12 (or 12a). However, a single kit may have multiple caps, and tubes 14 so locked therein, coded for the same or different size bottles. The visual coding along caps readily distinguishes different coded caps from each other in the system for using caps with different size bottles, and without requiring user observation of the length tubing 14 fixed to caps receivable in bottles to assure they reach or extend to the bottom thereof.

Figure 9:
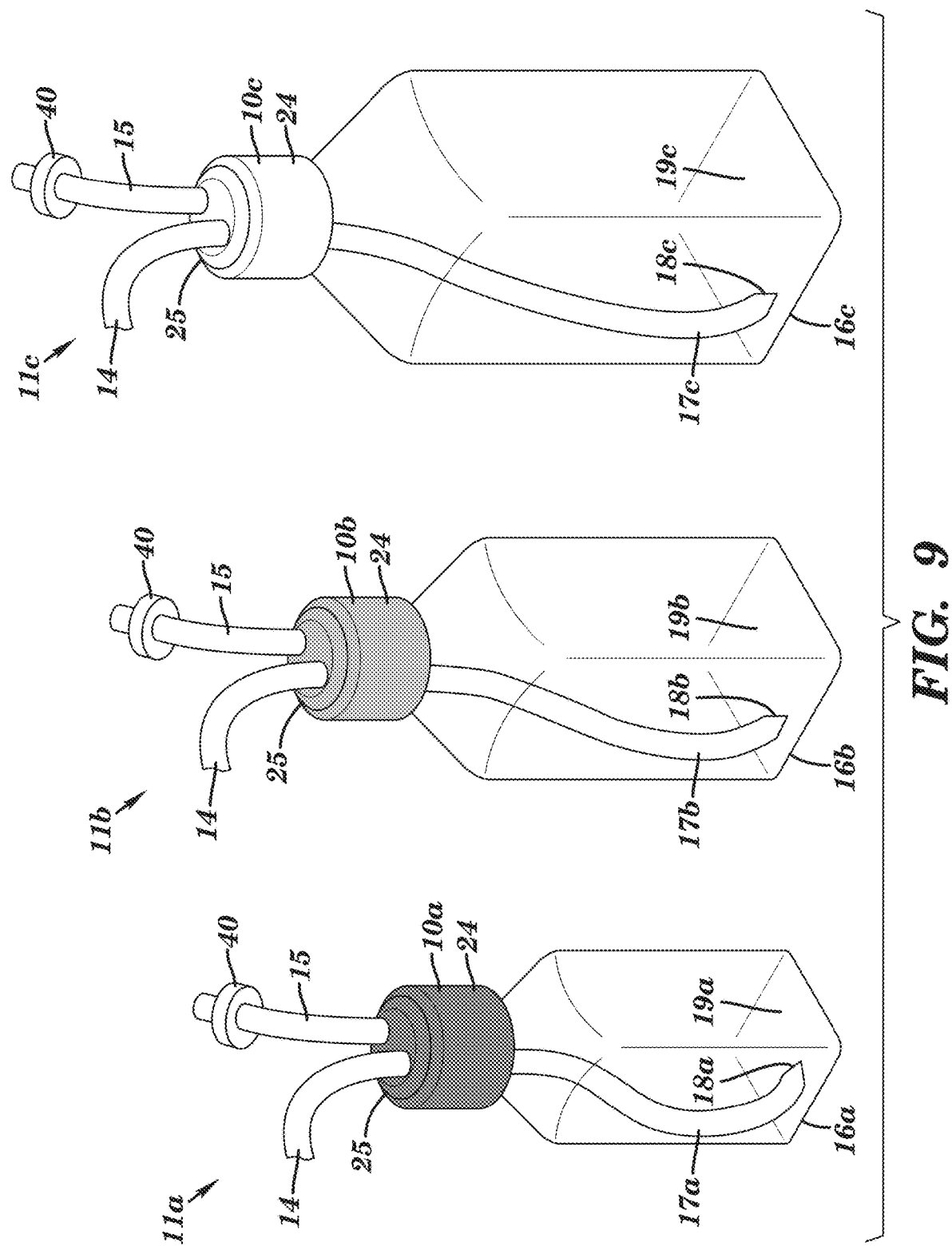
FIG. 9 is a perspective view of the apparatuses of FIGS. 7A, 7B, and 7C with example bottles engaged thereto.

FIGS. 7A, 7B, 7C, 8A, 8B, and 8C show an example of the system of the present invention with three different apparatuses 11 labelled 11a, 11b, and 11b each with a cap 10 labelled 10a, 10b, and 10b, and with a different tube 14 positionally fixed to the cap, as described above, to one of different length portion 17 labelled 17a, 17b, and 17c extending lengths L', L", and L'", respectively, to ends 18a, 18b, and 18c, respectively, for use with three different bottles which increase in size, as least in terms of the height dimension (H) of the bottle, as shown for example for three different ones of bottle 16 of FIG. 9 labelled 16a, 16b, and 16c.

As illustrated in FIG. 9, cylindrical body 24 of cap 10 is color coded to provide caps 10a, 10b, and 10c, such as for example being black for a 125 ml bottle 16a, orange for a 250 ml bottle 16b, and blue for a 500 ml bottle 16c, respectively, where lengths L', L", and L'" are 6, 7.5, and 8 inches, respectively. For purposes of illustration, colors are depicted in FIG. 9 by different shades of gray along cap 10a and 10b, and white in cap 10c, and tube 14 is shown truncated in extending from each of the caps away from their engaged example bottles. Other colors may be used, and additional caps of different colors, such as clear and white, may be used for 1 L and 2 L bottles, respectively. A chart is provided or made available to users which associates the color and/or indicia codes to different bottle sizes. This chart may be on a label attached, or printed upon, packaging of the above described kit. Although color is shown provided by material forming part of cap 10, i.e., body 24, the entire cap include portion 25 and body 24 may be of the same color code, or only portion 25 of the cap 10 is of elastomeric material which is color coded without body 24 being color coded.

Figure 10:
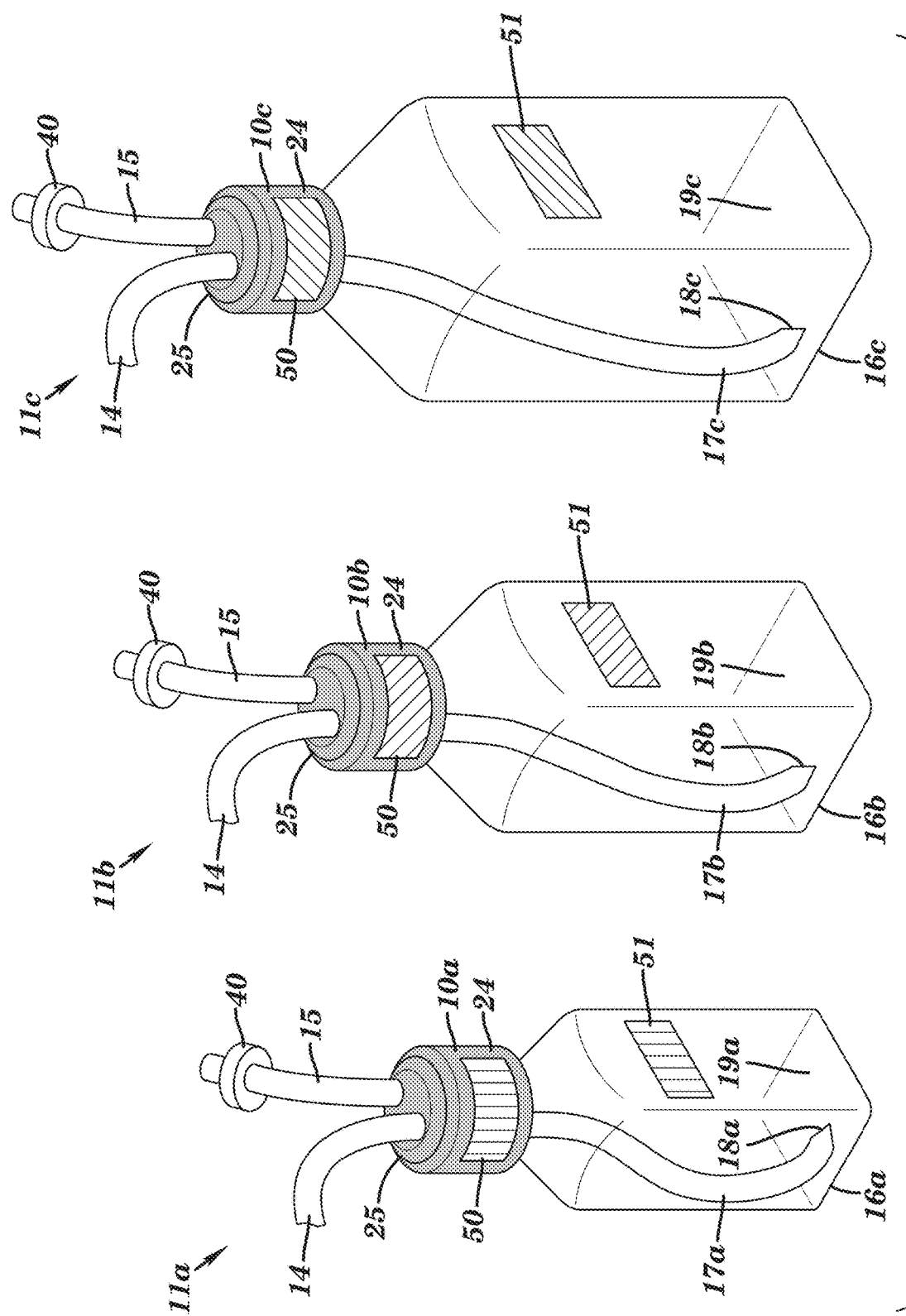
FIG. 10 is another perspective view of a system of the apparatuses of FIGS. 7A, 7B, and 7C with example bottles engaged thereto, where caps of the apparatuses are of the same color, caps are visually coded for different sized bottles using labels applied to the caps having different color and/or indicia denoted by different cross-hatching, and optional visual coding of bottles are shown using labels matching visual coding of caps.

Less preferably, different cap color is not used for visual coding, and an adhesive label 50 is used upon caps 10 with color indicia visually coding the caps 10 for different size bottles 16a, 16b, and 16c, in accordance with the tube 14 length along portions 17a, 17b, and 17c, as shown for example in FIG. 10. Each label 50 may be as thin strip of media, such paper or plastic with an adhesive material on one surface and printed/coated with ink on the opposite surface of the proper color indicium which can be attached along the cap's curved outer surface 27. For purposes of illustration, the different angular cross-hatching of labels 50 may each be considered as being indicative of a different color indicium, as the figure itself is not in color. Optional ridges 27a are removed from caps shown in FIGS. 7A, 7B, 7C, 8A, 8B, 8C, 9 and 10 for purposes of illustration, since different or no ridges may be provided along outer cap surface 27. However, when ridges 27a are present and labels 50 are used, each label 50 can be applied to proper coded cap below ridges 27a along smooth part of surface 27 of cap body 24. Optionally, additional or alternative indicium to color may be provided along labels 50. While caps 10a, 10b, and 10b are shown in FIGS. 7A, 7B, 7C, 8A, 8B, 8C, 9A, 9B, 9C, 10A, 10B, and 10C with cap 10 of FIGS. 1, 2, 3, 4A and 4B, caps 10a, 10b, 10c may be provided with one or more of the ports of FIG. 5C, 5D or 5E, and/or tube 14a and 14b of FIGS. 5C and 5D, if desired, where tube 14b is mounted to caps 10a, 10b, and 10c to extend respective lengths L', L", and L'".

The system of the present invention having apparatuses 11 with caps 10, such as caps 10a, 10b, and 10c of FIG. 9 or 10, visually coded for different sizes of bottle 16, such as bottle 16a, 16b, and 16c, reduces error in experimental setup and operation so that the proper caps are selected for bottles. Further, by visually inspecting caps 10 by their color codes it can be readily determined that tubes 14 providing the feeder lines to bottles of same or different sizes correctly extend internally in such bottles without having to check each and every feeder line.

Optionally, one or more of the bottles each has a matching visual coding along at least a portion, e.g., exterior surface of the bottle, as with those caps which are coded for use therewith. For example, the proper matching color may be provided by an adhesively applied label or strip 51 to bottles 16a, 16b, and 16c (similar or same as label 50) with same color as used on label 50 where labels 50 are used as depicted for example in FIG. 10 for coding caps 10a, 10b, and 10c. In a further example, labels 51 may also be applied to bottles 16a, 16b, and 16c in the example of FIG. 9, and each of the labels 51 have the respective different color which visually codes cap 10a, 10b, and 10c. The use of labels 51 provided along bottles 16 coded to their sizes, at least in terms of height, can further assist a user in properly selecting bottles 16a-c of proper size for engagement with their coded caps 10a, 10b, and 10c. Other means than labels 51 may also be used for providing a matching visual coding located along at least a portion of the bottle as those caps which are coded for use with such bottles, such as the entire material (e.g., molded plastic) forming bottles 16a, 16b, or 16c, or a portion thereof (such as molded texture along top end 20a below collar 36a) being same, or similar to, the different color which visually codes caps 10a, 10b, and 10c.

In FIG. 4B, the length L of the portion 17 of tube 14 (or tube 14b) to end 18 to interior surface 19 is slightly less than the height H of the bottle to account for the thickness of the bottle's bottom wall at closed bottle end 20b. While tube 14 (or 14a and 14b) and 15 are preferably flexible, such tubes are shown without any flexure(s) in FIGS. 1-3, 4A, 4B, 5B, 5C, 5D, 5E, 7A, 7B, 7C, 8A, 8B, and 8B. As shown in FIGS. 9 and 10, in order to assure portions 17a, 17b, and 17c of tube 14 (or 14b) extend in their respective apparatuses 11a, 11b, and 11c to interior bottom surfaces 19a, 19b, and 19c of any bottle 16a, 16b, and 16c coded by caps 10a, 10b, and 10c, the portion 17a, 17b, and 17c are selected of a length plus a tolerance or offset so that they each extends slightly longer than the height H dimension of the bottles coded for the caps. For example, such addition length tolerance may be in a range of 0.25 to 0.5 inches, but other tolerance may be used as desired. Thus, unlike as illustrated in FIGS. 1 and 4B, flexibility of tube 14 (or 14b) in bottle 16 allows its portion 17 to bend in bottle 16 so that end 18 lays upon, or extends along, the bottom interior 19 of the bottle, as shown for example by ends 18a, 18b, and 18c of portions 17a, 17b, and 17c, respectively, as depicted for example in FIGS. 9 and 10, coded for caps 10a, 10b, and 10c, respectively. Further, while preferably the apparatus 11 does not include the bottle 16 intended to be engaged thereto, such apparatus 11 may optionally further encompass the bottle. Thus, depending on the flexibility of tube 14 (or 14b), length L of its portion 17 is selected to be equal to the height H of the bottle 16 plus preferably a tolerance or offset to account for the flexibility of the tube to assure that the tube at least reaches or extends along, even substantially parallel to, the interior bottom of any of the bottles of the height to which the cap is coded for when engaging the cap, and without portion 17 being too long to end 18 as to undesirably risk bending of end 18 away from bottom end 20b.

From the foregoing description, it will be apparent that there has been provided a system, apparatus, and method for coding caps for different bottle sizes, and apparatuses in kits incorporating same. Variations and modifications in the herein described system, method, apparatuses, and kits will undoubtedly suggest themselves to those skilled in the art. Accordingly, the foregoing description should be taken as illustrative and not in a limiting sense.

The invention claimed is:
1. A system for coding caps for different bottle sizes comprising:

a plurality of caps having visual coding for use with different sizes of bottles at least in accordance with a height of the bottles, and each of said plurality of caps comprises a tube mounted to, or through, the cap to extend a selected length which enables one end of the tube to reach or extend along an interior surface of a closed bottom end of any of the bottles of said height to which the cap is coded for use therewith when engaging the cap, wherein said tube of at least one of said plurality of caps is flexible, and said selected length of the tube is determined in accordance with the height of any of the bottles to which the cap is coded for use therewith, said one end of the tube of said at least one of said plurality of caps bends to extend along a portion of the interior surface of the closed bottom end of any of the bottles of said height to which the cap is coded for use therewith when engaging the cap, and said one end of said tube of said at least one of said plurality of caps terminates in a non-square tip that avoids closure of said end of the tube by abutment with any of the bottles of said height to which the cap is coded for use therewith when engaging the cap.

2. The system according to claim 1 wherein each of said plurality of caps has one or more of color or indicia providing said visual coding for the cap.

3. The system according to claim 1 wherein each of said plurality of caps has a closed top end, an aperture extending through said closed top end into which said tube is mounted to extend there through, and means for fixing said tube with respect to the cap at said selected length after being extended through said aperture so that said end of said tube is configured to reach or extend along the interior surface of the closed bottom end of any of the bottles of said size to which the cap is coded for use therewith when engaging the cap.

4. The system according to claim 1 wherein each of said plurality of caps has at least a portion thereof which is of one of a plurality of different colors to provide said visual coding for the cap.

5. The system according to claim 1 wherein each of said plurality of caps comprises a generally cylindrical body shaped to form the cap with an open bottom end, and a closed top end with material, different from said body, having an aperture through which said tube extends and then mounted after passing through said open bottom end to extend to said one end of said tube.

6. The system according to claim 5 wherein each of said plurality of caps comprises a port to said aperture disposed along a top side of said closed top end, and said tube being received via said port to extend through said aperture, and said port being of said material to enable bonding of said tube by application of heat along at least a portion of said port to retain said tube with respect to the cap to said selected length after being extended through said aperture so that said end of said tube is configured to reach or extend along the interior surface of the closed bottom end of any of the bottles of said size to which the cap is coded for use therewith when engaging the cap.

7. The system according to claim 1 wherein each of said plurality of caps comprises a generally cylindrical body shaped to form the cap with an open bottom end and a closed top end having at least one aperture extending through said top end of the cap, said one end of said tube represents a first one of two ends of said tube, and a second one of said two ends of said tube is mounted in said aperture, via said open bottom end, so that extending said tube said selected length configures said first of said end of said tube to reach or extend along the interior surface of the closed bottom end of any of the bottles of said size to which the cap is coded for use therewith when engaging the cap.

8. The system according to claim 7 wherein each of said plurality of caps comprises a port to said aperture disposed along a top side of said closed top end of the cap, said tube represent a first tube, and a second tube has one end mounted in said port for communication with said first tube via said aperture.

9. The system according to claim 7 wherein said tube of each of said plurality of caps represents a first tube, and each of said plurality of caps further comprises:
 a port to said aperture disposed along a top side of said closed top end, in which said port has an exterior with a plurality of barbs; and
 a second tube having one end mounted over said port in engagement with said barbs.

10. The system according to claim 1 wherein each of said plurality of caps has an applied label having one or more of color or indicium to provide said visual coding for the cap.

11. The system according to claim 1 wherein each of said plurality of caps further comprises an air vent through the cap.

12. The system according to claim 1 wherein said tube of each of said plurality of caps represents a first of a pair of tubes mounted to extend through the cap, and when the cap engages one of said bottles coded for use with the cap a second of said pair of tubes provides an air vent to an interior of said one of said bottles.

13. The system according to claim 12 wherein said second of said pair of tubes has a filtering device mounted to filter air passing through said second of said pair of tubes.

14. The system according to claim 1 wherein one or more of the bottles each have means matching said visual coding located along at least a portion thereof as those ones of said plurality of caps which are coded for use with said one or more of the bottles.

15. A system for coding caps for different bottle sizes comprising:
 a plurality of caps having visual coding for use with different sizes of bottles at least in accordance with a height of the bottles, and each of said plurality of caps comprises a tube mounted to, or through, the cap to extend a selected length which enables one end of the tube to reach or extend along an interior surface of a closed bottom end of any of the bottles of said height to which the cap is coded for use therewith when engaging the cap, wherein each of said plurality of caps has an aperture extending through a closed top end of the cap into which said tube of the cap is mounted to extend there through and said tube has a circular cross-section which is maintained through said aperture at least until an opening of the tube at said one end, and at least bonding material along an interior of the aperture retains said tube to the cap after being extended through said aperture so that said end of said tube is configured to reach or extend along the interior surface of the closed bottom end of any of the bottles of said size to which the cap is coded for use therewith when engaging the cap.

16. The system according to claim 15 wherein said tube of each of said caps is flexible, and said selected length of the tube is determined in accordance with the height of any of the bottles to which the cap is coded for use therewith and any bending or flexing of said tube to further enable said one end of the tube to reach or extend along the interior surface of the closed bottom end of any of the bottles of said height to which the cap is coded for use therewith when engaging the cap.

17. The system according to claim 15 wherein each of said plurality of caps has one or more of color or indicia providing said visual coding for the cap.

18. The system according to claim 15 wherein each of said plurality of caps has at least a portion thereof which is of one of a plurality of different colors to provide said visual coding for the cap.

19. The system according to claim 15 wherein each of said plurality of caps has an applied label having one or more of color or indicium to provide said visual coding for the cap.

20. The system according to claim 15 wherein each of said plurality of caps further comprises an air vent through the cap.

21. The system according to claim 15 wherein said tube of each of said plurality of caps represents a first of a pair of tubes mounted to extend through the cap, and when the cap engages one of said bottles coded for use with the cap a second of said pair of tubes provides an air vent to an interior of said one of said bottles.

22. The system according to claim 15 wherein one or more of the bottles each have means matching said visual coding located along at least a portion thereof as those ones of said plurality of caps which are coded for use with said one or more of the bottles.

23. A system for coding caps for different bottle sizes comprising:
a plurality of caps having visual coding for use with different sizes of bottles at least in accordance with a height of the bottles, and each of said plurality of caps comprises a tube mounted to, or through, the cap to extend a selected length which enables one end of the tube to reach or extend along an interior surface of a closed bottom end of any of the bottles of said height to which the cap is coded for use therewith when engaging the cap, wherein each of said plurality of caps has an aperture extending through a closed top end of the cap into which said tube of the cap is mounted to extend there through and said tube has a circular cross-section which is maintained through said aperture at least until an opening of the tube at said one end, and at least one or more barbs along an interior of the aperture retains said tube to the cap after being extended through said aperture so that said end of said tube is configured to reach or extend along the interior surface of the closed bottom end of any of the bottles of said size to which the cap is coded for use therewith when engaging the cap.

24. The system according to claim 23 wherein each of said plurality of caps has one or more of color or indicia providing said visual coding for the cap.

25. The system according to claim 23 wherein said tube of each of said caps is flexible, and said selected length of the tube is determined in accordance with the height of any of the bottles to which the cap is coded for use therewith and any bending or flexing of said tube to further enable said one end of the tube to reach or extend along the interior surface of the closed bottom end of any of the bottles of said height to which the cap is coded for use therewith when engaging the cap.

26. The system according to claim 23 wherein one or more of the bottles each have means matching said visual coding located along at least a portion thereof as those ones of said plurality of caps which are coded for use with said one or more of the bottles.

27. A system for coding caps for different bottle sizes comprising:
a plurality of caps having visual coding for use with different sizes of bottles at least in accordance with a height of the bottles, and each of said plurality of caps comprises a tube mounted to, or through, the cap to extend a selected length which enables one end of the tube to reach or extend along an interior surface of a closed bottom end of any of the bottles of said height to which the cap is coded for use therewith when engaging the cap, wherein each of said plurality of caps has an aperture extending through a closed top end of the cap into which said tube of the cap is mounted to extend there through and said tube has a circular cross-section which is maintained through said aperture at least until an opening of the tube at said one end, and at least a clamp that mechanically couples said tube to the cap retains said tube to the cap after being extended through said aperture so that said end of said tube is configured to reach or extend along the interior surface of the closed bottom end of any of the bottles of said size to which the cap is coded for use therewith when engaging the cap.

28. The system according to claim 27 wherein each of said plurality of caps has one or more of color or indicia providing said visual coding for the cap.

29. The system according to claim 27 wherein said tube of each of said caps is flexible, and said selected length of the tube is determined in accordance with the height of any of the bottles to which the cap is coded for use therewith and any bending or flexing of said tube to further enable said one end of the tube to reach or extend along the interior surface of the closed bottom end of any of the bottles of said height to which the cap is coded for use therewith when engaging the cap.

30. The system according to claim 27 wherein one or more of the bottles each have means matching said visual coding located along at least a portion thereof as those ones of said plurality of caps which are coded for use with said one or more of the bottles.

\* \* \* \* \*